United States Patent
Selbie et al.

(10) Patent No.: US 6,202,475 B1
(45) Date of Patent: Mar. 20, 2001

(54) PREDICTING LOGARITHMIC REDUCTION VALUES

(75) Inventors: Michael R. L. Selbie, Lutherville, MD (US); Humphrey J. J. Drummond, London (GB); Warren T. Johnson, Grose Vale (AU)

(73) Assignee: USF Filtration and Separations Group, Inc., Timonium, MD (US)

( * ) Notice: Subject to any disclaimer, the term of this patent is extended or adjusted under 35 U.S.C. 154(b) by 0 days.

(21) Appl. No.: 09/386,899

(22) Filed: Aug. 31, 1999

Related U.S. Application Data

(63) Continuation of application No. PCT/AU98/00387, filed on May 26, 1998.

(51) Int. Cl.[7] ............................ G01N 15/08; B01D 61/00; B01D 46/42
(52) U.S. Cl. ............................ 73/38; 73/61.73; 73/64.47; 73/196; 210/650
(58) Field of Search .......................... 73/38, 61.73, 64.47, 73/196, 861.04, 863.23; 210/650, 321.84

(56) References Cited

U.S. PATENT DOCUMENTS

| | | | | |
|---|---|---|---|---|
| 4,614,109 | * | 9/1986 | Hoffmann | 73/38 |
| 4,656,865 | * | 4/1987 | Callan | 73/38 |
| 4,660,411 | * | 4/1987 | Reid | 73/38 |
| 4,718,270 | * | 1/1988 | Storr | 73/38 |
| 4,744,240 | * | 5/1988 | Reichelt | 73/38 |
| 4,797,211 | * | 1/1989 | Ehrfeld et al. | 210/321.84 |
| 4,846,970 | * | 7/1989 | Bertelsen et al. | 210/232 |
| 5,069,065 | * | 12/1991 | Sprunt et al. | 73/153 |
| 5,104,546 | * | 4/1992 | Filson et al. | 210/650 |
| 5,138,870 | * | 8/1992 | Lyssy | 73/38 |
| 5,297,420 | * | 3/1994 | Gilliland et al. | 73/38 |
| 5,353,630 | * | 10/1994 | Soda et al. | 73/38 |
| 5,361,625 | * | 11/1994 | Ylvisaker | 73/38 |
| 5,457,986 | * | 10/1995 | DiLeo et al. | 73/38 |
| 5,581,017 | * | 12/1996 | Bejtlich, III | 73/38 |

FOREIGN PATENT DOCUMENTS

| | | | |
|---|---|---|---|
| 3428307 | * | 2/1986 | (DE). |
| 2 253 572 | | 9/1992 | (GB). |
| 2 278 295 | | 11/1994 | (GB). |
| 06071120 | | 3/1994 | (JP). |

OTHER PUBLICATIONS

Copy of International Search Report (PCT/AU96/00144 by Examiner Olliey).

* cited by examiner

*Primary Examiner*—Hezron Williams
*Assistant Examiner*—David J. Wiggins
(74) *Attorney, Agent, or Firm*—Knobbe, Martens, Olson, and Bear LLP

(57) ABSTRACT

A method of predicting logarithmic reduction values for a membrane filtration system having a filtrate flow portion and a bypass flow portion relative to a filtrate permeable membrane with stable input gas flow comprising: determining the filtrate flow rate through the membrane under the action of an applied test pressure, determining the membrane bypass flow rate using integrity test measurements and estimating the logarithmic reduction value using the ratio of determined filtrate flow rate and determined bypass flow rate. Methods of testing the integrity of a porous membrane are also disclosed.

4 Claims, No Drawings

PREDICTING LOGARITHMIC REDUCTION VALUES

TECHNICAL FIELD

This application is a continuation of application Ser. No. PCT/AU98/00387, filed on May 26, 1998. The present invention relates to a method of predicting logarithmic reduction values in a filtration system and use of such values for control and monitoring of an operating filtration system.

BACKGROUND ART

The ability of a filtration system to remove particles is generally measured in terms of the logarithmic reduction value (LRV). For any given particles, the logarithmic reduction value is defined as:

$$LRV = \log_{10}\left(\frac{C_{inf}}{C_{eff}}\right) \quad (1)$$

where:

$C_{inf}$=Concentration of particle in the influent
$C_{eff}$=Concentration of particle in the effluent.

The particle used in the calculation can be any particle of interest, for example, in the case of disinfecting systems it would typically be bacteria or viruses, but may also be suspended solids.

DISCLOSURE OF THE INVENTION

The present invention provides a method of predicting logarithmic reduction values for a membrane filtration system comprising the following steps:

i) measuring the filtrate flow rate through the membrane;
ii) measuring the membrane bypass flow rate using integrity test measurements; and
iii) estimating the logarithmic reduction value using the ratio of measured filtrate flow rate and measured bypass flow rate as follows:

$$LRV = \log_{10}\left(\frac{Q_{filt}}{Q_{Bypass}}\right) \quad (2)$$

The applicant has developed a number of tests to determine the integrity of filtration membranes, these include the Diffusive Air Flow (DAF) and Pressure Decay Tests (PDT).

A preferred method of testing the integrity of a porous membrane comprises the steps of:

(i) wetting the membrane;
(ii) applying a gas pressure to one side of the membrane below the bubble point of the membrane pores; and
(iii) measuring gas flow across the membrane, said gas flow including diffusive flow through the membrane and flow through leaks and defects in the membrane, said gas flow being related to any defects in the membrane.

Preferably also, the gas flow is measured by monitoring the pressure decay of the gas pressure applied to the one side of the membrane. In another preferred form, the gas flow is measured by surrounding the other side of said membrane with a volume of fluid and measuring displacement of said fluid resulting from said gas flow.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to."

MODES FOR CARRYING OUT THE INVENTION

Preferred examples of these integrity tests will be described, by way of illustration only, as follows. If the lumens of a fully wetted membrane (i.e., all the pores are filled with liquid), are filled with air at a pressure below the bubble point, then the pores of the membrane will remain wet and there will be no significant air flow through the pores other than a relatively small flow due to diffusion. If a defect is present (such as a broken fiber), then air will flow through the defect, providing of course that the size of the defect is such that it has a bubble point below the test pressure. Therefore, the air flow in such a situation is related directly to the integrity of the membrane system. For an integral system, the air flow will be small and extremely difficult to measure directly. In order to simplify testing and to overcome this problem, the air flow is measured indirectly by measuring liquid flow (in the case of the DAF test) or by measuring pressure decay (in the case of the pressure hold/decay test).

In the Diffusive Air Flow test, the lumens are first pressurized with air to the test pressure (usually 100 kPa) keeping the feed-side of the membrane full. Once the test pressure has been reached the filtrate-side is sealed and the feed-side is opened via a measuring valve which can measure liquid flow therethrough. Initially, there is rapid liquid flow through the valve. The high initial flow is predominantly due to the volume of water displaced by membrane expansion and that displaced by water moving to the extremities of the pores of the membrane.

After the initial period, the flow drops to a more stable level and the residual liquid flow is solely due to liquid being displaced by diffusive air flow and air flow through any defects. This air flow is the DAF measurement and is typically volume per unit time.

Diffusive air flow is the flow of air through an integral wetted membrane caused by dissolved air transport through the membrane. The driving force for dissolved air diffusion is the differential partial pressure across the wet membrane. As the solubility of air increases with pressure, there is a higher concentration of dissolved air in the liquid layer. The system tends to equalize the concentration in the water layer, which results in a steady-state air transport across the membrane. At the low pressure side (feed-side), the lower partial air pressure allows the air to continuously leave solution. The released air builds up at the top of the feed-side, and there is an accompanying flow of displaced water through the feed side measuring valve.

Defects in the membrane are considered to be "holes" in the membrane that, in effect, penetrate the full width of the walls of the membrane. Air flow through defects is caused by "viscous" gas flow. This means that the air simply flows through a defect, initially replacing the water in the defect. The replacement of water in a defect is relatively easy since defects, by definition, are large compared to the pores and thus have a much lower bubble point (less capillary action). The air flow through defects is related to the size of the defects, and also the number of defects.

Air flow caused by leakage around o-rings is another cause of high flows of air in the DAF measurement.

The DAF measurement is therefore the sum of two components, the diffusive air flow through the membranes (good) and the flow of air through defects in the membranes and o-ring leaks (bad). For any particular filter type, the diffusive air flow through the membranes can be both calculated and measured. By comparing a DAF measurement with the expected value for a fully integral filter, an indication of the relative integrity of the filter can be determined.

In the pressure decay test, as with the DAF test, the lumens are first pressurized with air to the test pressure keeping the feed-side of the membrane full. Once the test pressure has been reached, the filtrate side is sealed and the feed-side vented to atmosphere. The drop in pressure of the filtrate system with time is then monitored. This pressure decay will be directly related to air flow across the membrane and hence system integrity, assuming no leaks elsewhere.

In the DAF test what is measured is the air flow through a membrane. This is normally assumed to be just air flow through defects in the membrane. This air flow through defects can be related to a liquid flow through the same defects, under operating conditions. By comparing the liquid flow through defects and the liquid flow through membrane during filtration, an accurate prediction of a logarithmic reduction value can be calculated from the following equation:

$$LRV = \log_{10}\left(\frac{Q_{l,filt}}{Q_{l,DAF}}\right) \quad (3)$$

where:

$Q_{l,filt}$=the liquid flow through the membrane during filtration (and at the DAF test pressure); and $Q_{l,DAF}$=the equivalent liquid flow through defects under operating conditions calculated from the DAF test measurements.

The equivalent value of liquid flow through a defect $Q_{l,DAF}$ can be calculated from the measured DAF result, that is, the air flow through the defect. A DAF test is conducted at a set pressure, known as the test pressure $P_{test}$. The downstream side of the membrane is vented to atmosphere, and has an atmospheric pressure $P_{atm}$. When air travels through the membrane via a defect, it expands since the test pressure is greater than atmospheric pressure encountered on the downstream side. Hence, the volume of water displaced from the downstream side during a DAF test reflects the volume of air passing through the membrane at atmospheric pressure.

Given the above, a simple means can be devised for correcting for the pressure differences on either side of the membranes when calculating $Q_{l,DAF}$ from $Q_{a,DAF}$ (air flow through the defect). First, from the measured volume air flow through the defect, a mass flow of air through the membrane can be calculated. This air mass flow can then be converted back to a volume flow on the downstream side of the membrane.

A defect is considered as a cylindrical hole through the membrane. This may not strictly be the case, but is a good assumption and allows model calculation of flow through a defect. So long as there is laminar flow and the length of the defect is at least, say, ten times its diameter, the measured volume of air flow through a cylindrical defect ($Q_{V,a,defect}$) can be described by the Hagen-Poiseuille equation:

$$Q_{V,a,defect} = \frac{\pi d^4 (P_{test} - P_{atm})}{128 \eta_a l} \quad (4)$$

where:

d=the defect diameter;

$P_{test}$=the test (upstream) pressure;

$P_{atm}$=the atmospheric (downstream) pressure during the DAF test;

$\eta_a$=the viscosity of air at the temperature of filtration; and l=the thickness of the membrane.

The mass flow of air through the defect can be related by the volume flow air with density correction.

$$Q_{m,a,defect} = \rho Q_{V,a,defect} \quad (5)$$

where:

$\rho$=the density of the air in the membrane.

The density of air can be calculated from the ideal gas equation:

$$\rho = \frac{PM}{RT} \quad (6)$$

where:

P=the pressure;

M=the molecular weight of air;

R=the gas constant; and

T=the temperature.

The pressure is a difficult parameter to determine for the membrane situation since there is a constant pressure gradient across the membrane, from $P_{test}$ to $P_{atm}$. A simple way of dealing with this problem is to use the mean pressure.

$$P = \frac{P_{test} + P_{atm}}{2} \quad (7)$$

From equations 5–8, the mass flow of air through a defect is given by:

$$Q_{m,a,defect} = \frac{\pi d^4 (P_{test}^2 - P_{atm}^2)}{256 \eta_a l} \frac{M}{RT} \quad (8)$$

Now given that the volume of water displaced by the air is at the downstream side, the volume of air that needs to be considered can be calculated from the air mass flow through the defect at atmospheric (downstream) pressure.

Given that, from the ideal gas equation:

$$P_{atm} = \frac{\rho RT}{M} \quad (9)$$

Combining equations 5, 8 and 9 we find:

$$Q_{V,a,defect} = \frac{\pi d^4 (P_{test}^2 - P_{atm}^2)}{256 \eta_a l P_{atm}} \quad (10)$$

The Hagen-Poiseuille equation can also be used to calculate the liquid flow through a defect. The equation for liquid flow is simply the same as the equation for air flow given by equation 4. Since the liquid used is generally water, which is incompressible, none of the considerations of pressure as needed for the air flow, need to be considered. The volume liquid flow through the same defect as above is given by:

$$Q_{V,l,defect} = \frac{\pi d^4 TMP}{128 \eta_1 l} \quad (11)$$

where the TMP is the trans-membrane pressure, i.e., the operating pressure of filtration, which is just equal to the pressure difference across the membrane during filtration.

Comparing equations 10 and 11, we find that liquid volume flow through the defect at operational TMP is given by:

$$Q_{V,l,defect} = Q_{V,a,defect} \frac{\eta \alpha}{\eta l} \frac{2P_{test}TMP}{(P_{test}^2 - P_{atm}^2)} \quad (12)$$

Note that $Q_{V,l,defect}$ can be calculated from experiment since $Q_{V,a,defect}$ is just the measured DAF flow, and the rest of the parameters in equation 12 are either known or easily measured.

The measured $Q_{V,l,defect}$ can be used to calculate LRV values. From equation 3, the LRV is given by:

$$LRV = \log_{10}\left(\frac{Q_{V,l,filt}}{Q_{V,l,defect}}\right) \quad (13)$$

where $Q_{V,l,filt}$ is just the flow through the membrane in normal filtration mode. Combining equations 12 and 13, the LRV can then be calculated in the following from:

$$LRV = \log_{10}\left(\frac{Q_{V,l,filt}\eta_1(P_{test}^2 - P_{atm}^2)}{Q_{V,a,defect}\eta_a 2P_{atm}TMP}\right) \quad (14)$$

Note that all parameters in equation 14 are directly measurable.

The bypass flow may also be determined as follows assuming the air flow measured in the DAF test is due to leakage through defects in the membrane and filter seals:

$$Q_{bypass} = Q_{DAF} \times \frac{2\mu_{air}P_{filt}P_{vent}}{\mu_{filt}(P_{test}^2 - P_{vent}^2)} \quad (15)$$

where:
$Q_{bypass}$=Equivalent bypass liquid flow
$Q_{DAF}$=Bypass airflow as measured using DAF test
$\mu_{air}$=Viscosity of air
$\mu_{filt}$=Viscosity of filtrate fluid (usually water during test)
$P_{test}$=DAF Test pressure, absolute
$P_{vent}$=DAF Vent pressure, absolute, usually atmospheric
$P_{filt}$=Filtration transmembrane pressure
The log reduction value can then be estimated as follows:

$$LRV = \log_{10}\left(\frac{Q_{filt}}{Q_{DAF}} \times \frac{\mu_{filt}(P_{test}^2 - P_{vent}^2)}{2\mu_{air}P_{filt}P_{vent}}\right) \quad (16)$$

where $Q_{filt}$=Filtrate flow rate As with the DAF Test, it is possible to estimate the log reduction value from the pressure decay results. The only additional information required is the pressurized volume of the filtrate pipework during the pressure decay test for the given system. Bypass flow can be estimated from the following equation:

$$Q_{bypass} = \frac{\Delta P V_{filt}}{P_{atm}t} \times \frac{2\mu_{air}P_{filt}P_{vent}}{\mu_{filt}(P_{test}^2 - P_{vent}^2)} \quad (17)$$

where:
$\Delta P$=Pressure decay measured over time t
$V_{filt}$=Volume of filtrate system under test pressure
$P_{atm}$=Atmospheric Pressure
$\mu_{air}$=Viscosity of air
$\mu_{filt}$=Viscosity of filtrate fluid (usually water during test)
$P_{test}$=Test pressure, absolute
$P_{vent}$=Vent pressure, absolute, usually atmospheric
$P_{filt}$=Filtration transmembrane pressure
As with the DAF test logarithmic reduction values can be predicted from the bypass flow rate by comparison with the filtrate flow rate by as follows:

$$LRV = \log_{10}\left(Q_{filt} \times \frac{P_{atm}t}{\Delta P V_{filt}} \times \frac{\mu_{filt}(P_{test}^2 - P_{vent}^2)}{2\mu_{air}P_{filt}P_{vent}}\right) \quad (18)$$

where $Q_{filt}$=Filtrate flow rate

The DAF and PDT tests can be automated to provide regular process monitoring of system integrity during operation. Further, these tests are highly sensitive and enable system integrity to be directly monitored without the requirement for complex water testing. The predicted logarithmic reduction values can be used to monitor and control system performance and loss of integrity. System control can be provided by comparing desired or required LRV's with the predicted LRV's for a particular system and adjusting system performance in response to such comparison.

It will be appreciated that further embodiments and exemplifications of the invention are possible without departing from the spirit or scope of the invention described.

What is claimed is:

1. A method of predicting a logarithmic reduction value for a membrane filtration system, the membrane filtration system having a membrane, the membrane having a bubble point, a first side, and a second side, and the logarithmic reduction value being defined by the formula:

$$LRV = \log_{10}\left(\frac{C_{inf}}{C_{eff}}\right) \quad (1)$$

wherein LRV is the logarithmic reduction value, $C_{inf}$ is a concentration of particle in an influent, and $C_{eff}$ is a concentration of particle in an effluent, the method comprising the following steps:

(i) measuring a flow rate of liquid filtrate through the membrane;

(ii) measuring a membrane bypass flow rate using an integrity test measurement, wherein the membrane bypass flow rate is the flow rate through leaks and defects in the membrane; and (iii) estimating the logarithmic reduction value using a ratio of the filtrate flow rate and the membrane bypass flow rate as follows:

$$LRV_{est} = \log_{10}\left(\frac{Q_{filt}}{Q_{bypass}}\right),$$

wherein $LRV_{est}$ is an estimate of the logarithmic reduction value, $Q_{filt}$ is the filtrate flow rate, and $Q_{bypass}$ is the membrane bypass flow rate.

2. The method of claim 1 wherein said integrity test method comprises the steps of:
  (i) wetting the membrane;
  (ii) applying a gas pressure to the first side of the membrane below the bubble point of the membrane;
  (iii) measuring a gas flow across the membrane, said gas flow including a diffusive flow through the membrane and a flow through leaks and defects in the membrane; and
  (iv) determining the flow through leaks and defects in the membrane by subtracting the diffusive flow through the membrane, said diffusive flow being determined by a calculation or a measurement of a fully integral membrane, said gas flow through leaks and defects in the membrane being indicative of the membrane bypass flow rate.

3. The method according to claim 2 wherein the gas flow is measured by monitoring a temporal decay of the gas pressure applied to the first side of the membrane.

4. The method according to claim 2 wherein the gas flow is measured by surrounding the second side of said membrane with a volume of a fluid and measuring a displacement of said fluid resulting from said gas flow.

* * * * *

UNITED STATES PATENT AND TRADEMARK OFFICE
CERTIFICATE OF CORRECTION

PATENT NO. : 6,202,475 B1
DATED : March 20, 2001
INVENTOR(S) : Michael R. Selbie, Humphrey J.J. Drummond Warren T. Johnson It is certified that error appears in the above-identified patent and that said Letters Patent is hereby corrected as shown below:

Foreign Application Priority Data

May 30, 1997 [AU]   Australia......................PO 7097

Signed and Sealed this

Twenty-eighth Day of August, 2001

*Attest:*

NICHOLAS P. GODICI
*Attesting Officer*          *Acting Director of the United States Patent and Trademark Office*